(12) United States Patent
Nordström et al.

(10) Patent No.: US 11,465,000 B2
(45) Date of Patent: Oct. 11, 2022

(54) TREATMENT PLANNING

(71) Applicant: Elekta Instrument AB, Stockholm (SE)

(72) Inventors: Håkan Nordström, Sollentuna (SE); Joakim Wang Erlandsson, Stockholm (SE); Fredrik Lundqvist, Järfalla (SE); Marcus Hennix, Huddinge (SE); Björn Somell, Stockholm (SE)

(73) Assignee: Elekta Instrument AB

( * ) Notice: Subject to any disclaimer, the term of this patent is extended or adjusted under 35 U.S.C. 154(b) by 187 days.

(21) Appl. No.: 16/806,004

(22) Filed: Mar. 2, 2020

(65) Prior Publication Data
US 2021/0268314 A1 Sep. 2, 2021

(51) Int. Cl.
*A61N 5/10* (2006.01)

(52) U.S. Cl.
CPC ......... *A61N 5/1071* (2013.01); *A61N 5/1067* (2013.01); *A61N 5/1084* (2013.01)

(58) Field of Classification Search
CPC .. A61N 5/1071; A61N 5/1084; A61N 5/1067; A61N 5/103; A61N 5/1042; A61N 5/1045; A61N 5/1047; A61N 5/1048; A61N 5/1077
See application file for complete search history.

(56) References Cited

U.S. PATENT DOCUMENTS

| | | | |
|---|---|---|---|
| 6,201,988 B1* | 3/2001 | Bourland | A61N 5/1031 378/65 |
| 9,358,404 B2* | 6/2016 | Danielsson | A61N 5/103 |
| 2005/0109939 A1* | 5/2005 | Engler | G01J 1/00 250/336.1 |
| 2018/0085596 A1* | 3/2018 | Peltola | A61N 5/103 |
| 2020/0289850 A1* | 9/2020 | Wosle | A61N 5/1049 |

OTHER PUBLICATIONS

Rui Liao, Jeffery A. Williams, Lee Myers, Shidon Li, Russell H. Taylor & Christos Davatzikos (2000) Optimization of Multiple-Isocenter Treatment Planning for Linac-Based Stereotactic Radiosurgery, Computer Aided Surgery, 5:4, 220-233, DOI: 10.3109/10929080009148891 (Year: 2000).*

* cited by examiner

*Primary Examiner* — Carrie R Dorna
(74) *Attorney, Agent, or Firm* — Burr & Forman LLP; Jeffrey H. Kamenetsky

(57) ABSTRACT

The present invention relates to the field of radiation therapy and methods, software and systems for treatment planning. A target volume of a region of a patient to be treated during a treatment of a patient in a radiation therapy unit is obtained. A first isocenter location procedure is performed including inter alia evaluating potential isocenter locations along normal directions of the surface and respective iso-distance surfaces in respective starting voxels in a direction inwards from the surface, and a second isocenter location procedure is performed including inter alia identifying a median axis of the target volume or center point of the target volume, placing isocenters at locations along the median axis, and placing isocenters in the target volume based on a distance to existing isocenters and to the target surface.

27 Claims, 14 Drawing Sheets

TREATMENT PLANNING

FIELD OF THE INVENTION

The present invention relates to the field of radiation therapy and to systems, methods and modules for planning a treatment session of a patient by means of a radiation therapy system comprising a radiation therapy unit having a fixed radiation focus point. In particular, the present invention relates to systems, methods and modules for determining the locations of isocenters in a target volume.

BACKGROUND OF THE INVENTION

The development of surgical techniques has made great progress over the years. For instance, for patients requiring brain surgery, non-invasive surgery is now available which is afflicted with very little trauma to the patient.

One system for non-invasive surgery is the Leksell Gamma Knife® Perfexion system, which provides such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all or some radiation sources intersect or converge, causing the radiation to reach tissue-destructive levels. The point of convergence is hereinafter referred to as the "focus point".

Treatment planning optimization for radiation therapy, including for example gamma knife radio-surgery, aims at maximizing the dose delivered to the target volume within the patient (e.g. in treatment of tumors) at the same time as the dose delivered to adjacent normal tissues is minimized. In treatment planning optimization, the delivered radiation dose is limited by two competing factors where the first one is delivering a maximum dose to the target volume and the second one is delivering the minimum dose to the surrounding normal tissues.

The treatment planning optimization is a process including optimizing the number of shots being used (i.e. number of doses being delivered), the shot size, the shot time, and the position of the shot. Clearly, the irregularity and size of a target volume greatly influence the number of shots needed and the size of the shots being used to optimize the treatment. Normally, the process includes obtaining a three-dimensional representation of the target (e.g. by non-invasive image capturing by X-ray) for the radiation therapy and filling the target with spheres representing the shots without extending area strongly dosed by radiation greatly outside the target and without limited overlapping between shots). It has been shown that in order to preserve dose homogeneity (even coverage of for example an isodose level of 50%) and in a multi-shot plan, shots should not overlap with each other in a too great extent. Thus, overlapping shots may destroy the desired dose homogeneity inside the target. Further, shots protruding outside the target may result in excessive dose to surrounding normal tissues. This requires, for targets of identical volume yet different shapes, use of small shots for complicated contours (i.e. for targets having an irregular shape) and larger shots for regular shapes.

A pre-requisite in convex plan optimization, so called sector duration optimization (SDO) for the Leksell Gamma Knife, is that the isocenter locations are fixed. Several methods have been proposed over the years to find a viable set of locations. A common feature of all these algorithms is that the target volume is geometrically filled with several 3D shapes that are proxies for real dose distributions of the shots. However, as a result of SDO the dose delivered from each isocenter is a weighted sum of shots; the collimator configuration and the weight of each shot are not known a priori. Therefore, basing isocenter locations on a poor description of dose distributions will irrevocably lead to a sub-optimal solution.

In U.S. Pat. No. 6,201,988 to Bourland et al, such an optimization procedure is disclosed. Medial axis transformation (so called skeletonization) is used to characterize the target shape and to determine the shot parameters (i.e. position, collimator size and weight). According to U.S. Pat. No. 6,201,988, only skeleton points are considered for potential shot positions and the corresponding shot size is provided by the skeletonization. The shots are represented by spheres and are modeled as discs in filling process. The endpoints of the skeleton are used as start-points in the filling process. However, the treatment planning optimization shown in U.S. Pat. No. 6,201,988 may provide treatment plans having a non-optimal distribution of shot sizes, for example, an unnecessary large amount of small shot sizes may be included leading to many shots being used.

Another heuristic approach is template matching where templates representing compact dose distributions (so called shots) are placed as to touch the target volume periphery, without overlapping other shots too much. When no more such shot positions exist the volume covered so far is treated as non-target, and the procedure is repeated with the reduced target volume. Thus, the target is filled from the surface and inwards, trying to place as large shots as possible at each iteration. This approach is described in the U.S. Pat. No. 9,358,404 to Elekta AB.

However, there is still a need of more efficient methods for planning the treatment and for optimizing the treatment planning.

SUMMARY OF THE INVENTION

An object of the present invention is to provide more efficient methods, systems and modules for planning the treatment and thus for optimizing the treatment planning.

A further object of the present invention is to provide more efficient methods, systems and modules for determining isocenter positions or locations in a target volume during a treatment planning procedure.

These and other objects are fulfilled by the present invention as defined by the independent claims. Preferred embodiments are defined by the dependent claims.

The term "target volume" refers to a representation of a target of a patient to be treated during radiation therapy. The target may be a tumour to be treated with radiation therapy. Typically, the representation of the target is obtained by, for example, non-invasive image capturing using X-ray or NMR.

The term "shot" refers to a delivery of radiation to a predetermined position within a target volume having a predetermined level of radiation and a spatial distribution. The shot is delivered during a predetermined time ("beam-on" time) via at least one sector of the collimator of the therapy system using one of the states of the sector. A "composite shot" refers to the delivery of radiation to a focus point using different collimator sizes for different sectors.

The term "beam-on time" refers to the predetermined time during which a shot is delivered to the target volume.

The term "overlapping" means that, in viewing the shots as 3-D volumes (defined as the volume with dose above a selected threshold, e.g. the 50% isodose level), a shot volume overlaps or intersects other shot volumes.

The present invention can, for example, be used in radiation therapy or radiotherapy. Radiotherapy is used to treat cancers and other ailments in mammalian (e.g., human and animal) tissue. One such radiotherapy device or a radiation therapy device is a Gamma Knife, which irradiates a patient with many low-intensity gamma rays that converge with high intensity and high precision at a target (e.g., a tumor). Another radiotherapy device uses a linear accelerator, which irradiates a tumor with high-energy particles (e.g., photons, electrons, and the like). Still another radiotherapy device, a cyclotron, uses protons and/or ions. The direction and shape of the radiation beam should be accurately controlled to ensure that the tumor receives the prescribed radiation dose, and the radiation from the beam should minimize damage to the surrounding healthy tissue, often called the organ(s) at risk (OARs). Treatment planning can be used to control radiation beam parameters, and a radiotherapy device effectuates a treatment by delivering a spatially varying dose distribution to the patient.

The present invention is for example used in connection with treatment planning of treatment provided by means of a radiation therapy systems having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

A planning process generally involves the examination (mapping, non-invasive image capturing, as for example by X-ray or NMR) of a target volume for radiation therapy, fill the target, without extending areas strongly dosed by radiation too much outside the target, determining a level of radiation which is therapeutically effective when directed into volumes of the target which are to be treated, determination a distribution of shots or doses of radiation which can be directed into the target such that radiation within each shot which exceeds a predetermined percentage of the level of radiation which is therapeutically effective by more than a fixed percentage of each shot of the radiation, is not directed at areas outside the target.

The present invention takes a new and different approach to treatment planning. Instead of using pre-defined dose distributions as the starting point or user defined dose distributions, isocenter locations are automatically determined based on geometrical features of the target such as the curvature of the surface and its morphology.

According to an aspect of the present invention, there is provided a method for dose planning for a radiation therapy system. The system comprises a radiation therapy unit having a fixed radiation focus point, wherein a spatial dose distribution surrounding the focus point can be changed by adjusting collimator settings or adjusting the leaves in a MLC (multi leaf collimator). The collimator has a plurality of collimator passage inlets for directing radiation emanating from radioactive sources of a source carrier arrangement of the therapy system to the focus point. The method comprises:

a) obtaining a target volume of a region of a patient to be treated during a treatment of a patient in a radiation therapy unit, the target volume, for example, being modeled as a three-dimensional voxel representation;

b) calculating a curvature of the target surface;

c) performing a first isocenter location procedure including:

c1) selecting starting voxels on the surface of the target based on selection curvature criteria, c2) evaluating potential isocenter locations along normal directions of the surface and respective isodistance surfaces in respective starting voxels in a direction inwards from the surface, wherein the normal directions are subsequently calculated from the surface of the target to respective isodistance surfaces inwards from respective surface;

c3) selecting a location along the normal directions for placing of an isocenter, d) performing a second isocenter location procedure including:

d1) identifying a median axis of the target volume or center point of the target volume, d2) placing isocenters at locations along the median axis, d3) placing isocenters in the target volume based on a distance to existing isocenters and to the target surface, and e) providing an isocenter location distribution in the target based on the isocenters placed in the target volume in the first and second isocenter location procedures.

The present invention is based on the insight that the geometry of a target can be used to form basis for the isocenter location procedure. Thus, instead of using pre-defined dose distributions as starting points, the isocenter locations are determined from geometrical features of the target, such as the curvature of the surface and its morphology.

In an embodiment of the present invention, step d) further comprises the step of determining a center of mass of the target volume and placing an isocenter at the center of mass.

In an embodiment, step d3) further comprises the step of placing isocenters in the target volume based on a relative distance to existing isocenters and to the surface, including: determining the relative distance to an isocenter as the distance from a potential isocenter location to that isocenter divided by an isocenter cut off distance constant, and determining the relative distance to the surface as the Euclidian distance from the potential isocenter location divided by a surface cut off distance constant.

According to an embodiment, the minimum of the relative distance to a closest isocenter and the relative distance to the surface for each potential location are compared with corresponding minimum relative distance in all other potential locations and the maximum relative distance is selected as an isocenter location.

In embodiments of the present invention, isocenter placement is stopped when no further potential isocenter location with a relative distance greater than a pre-determined constant could be found.

According to embodiments, step c3) further comprises: selecting a location along the normal directions for placing of an isocenter when predetermined conditions are met, wherein the predetermined conditions include:

i) a total distance along the normal direction is greater or equal to a distance proportional to the curvature radius of the surface at the starting voxel; or ii) the distance to the surface along the normal direction is no longer increasing.

In embodiments, step c1) selecting starting voxels on the surface of the target based on selection curvature criteria, further comprises: identifying potential starting voxels on the surface where a curvature radius is less than a predetermined threshold value; and selecting starting voxels among potential starting voxels by iterative selection based on maximum curvature and disregarding starting voxels that are within pre-defined distance from already chosen starting voxels.

According to embodiments of the present invention, step e) providing an isocenter location distribution in the target based on the isocenters placed in the target volume in the first and second isocenter location procedures further comprises performing an isocenter reduction procedure including determining a radius to adjacent isocenters from a certain isocenter and removing isocenters being within a predetermined radius boundary.

In yet other embodiments of the present invention the step of removing isocenters being within a predetermined radius boundary includes replacing all isocenters within a certain volume surrounding at least one isocenter with a candidate isocenter. For example, the isocenter located at a point with the highest curvature, or at the longest distance from the surface is selected as candidate isocenter.

According to further embodiments of the present invention, the certain volume surrounding at least one isocenter is a radius boundary.

Yet other embodiments of the present invention include in step d2) identifying a subset of the target voxels as potential isocenter points, calculating the normal directions from the target surface inwards for each of the potential isocenter points, moving the potential isocenter point inwards a small distance along the normal to a new isodistance surface, and calculating the normal of the isodistance surface and moving the potential isocenter point inwards along the normal until the distance to the surface is no longer increasing, selecting that potential location as an isocenter location.

According to embodiments of the present invention, a pre-processing step including smoothing a target surface using a filter function is performed.

In embodiments the filter function uses a 3D Gaussian filter kernel.

According to another aspect of the present invention, there is provided a dose planning software for determining isocenter locations in a target volume for use at a radiation therapy system, the system comprising a radiation therapy unit having a fixed radiation focus point, wherein a spatial dose distribution surrounding the focus point can be changed, wherein radiation is directed to the focus point. The dose planning software is configured to execute:

a) obtaining a target volume of a region of a patient to be treated during a treatment of a patient in a radiation therapy unit, the target volume, for example, being modeled as a three-dimensional voxel representation;

b) calculating a curvature of the target surface;

c) performing a first isocenter location procedure including:

c1) selecting starting voxels on the surface of the target based on selection curvature criteria, c2) evaluating potential isocenter locations along normal directions of the surface and respective isodistance surfaces in respective starting voxels in a direction inwards from the surface, wherein the normal directions are subsequently calculated from the surface of the target to respective isodistance surfaces inwards from respective surfaces;

c3) selecting a location along the normal directions for placing of an isocenter, d) performing a second isocenter location procedure including:

d1) identifying a median axis of the target volume or center point of the target volume, d2) placing isocenters at locations along the median axis, d3) placing isocenters in the target volume based on a distance to existing isocenters and to the target surface, and e) providing an isocenter location distribution in the target based on the isocenters placed in the target volume in the first and second isocenter location procedures.

According to an embodiment of the dose planning software, step d) further comprises the step of determining a center of mass of the target volume and placing an isocenter at the center of mass.

In embodiments of the present invention, step d3) further comprises the step of placing isocenters in the target volume based on a relative distance to existing isocenters and to the surface, including: determining the relative distance to an isocenter as the distance from a potential isocenter location to that isocenter divided by an isocenter cut off distance constant, and determining the relative distance to the surface as the Euclidian distance from the potential isocenter location divided by a surface cut off distance constant.

According to embodiments of the present invention, the dose planning software is configured to execute: comparing the minimum of the relative distance to a closest isocenter and the relative distance to the surface for each potential location with corresponding minimum relative distance in all other potential locations; and selecting the maximum relative distance as an isocenter location.

In yet other embodiments of the present invention, the dose planning software is configured to execute: stopping isocenter placement when no further potential isocenter location with a relative distance greater than a pre-determined constant could be found.

According to embodiments of the present invention, step c3) further comprises: selecting a location along the normal directions for placing of an isocenter when predetermined conditions are met, wherein the predetermined conditions include a total distance along the normal direction is greater or equal to a distance proportional to the curvature radius of the surface at the starting voxel; or the distance to the surface along the normal direction is no longer increasing.

In embodiments of the present invention, step c1) selecting starting voxels on the surface of the target based on selection curvature criteria, further comprises: identifying potential starting voxels on the surface where a curvature radius is less than a predetermined threshold value; and selecting starting voxels among potential starting voxels by iterative selection based on maximum curvature, and disregarding starting voxels that are within pre-defined distance from already chosen starting voxels According to yet other embodiments, step e) providing an isocenter location distribution in the target based on the isocenters placed in the target volume in the first and second isocenter location procedures further comprises performing an isocenter reduction procedure including: determining a radius to adjacent isocenters from a certain isocenter and removing isocenters being within a predetermined radius boundary.

In embodiments of the present invention, the step of removing isocenters being within a predetermined radius boundary includes replacing all isocenters within a certain volume surrounding at least one isocenter with a candidate isocenter. For example, the isocenter located at a point with the highest curvature, or at the longest distance from the surface is selected as candidate isocenter.

According to yet other embodiments, the certain volume surrounding at least one isocenter is a radius boundary.

In embodiments of the present invention, step d2) placing isocenters at locations along the at least one median axis further comprises: identifying a subset of the target voxels as potential isocenter points, calculating the normal directions from the target surface inwards for each of the potential isocenter points, moving the potential isocenter point inwards a small distance along the normal to a new isodistance surface, and calculating the normal of the isodistance surface and moving the potential isocenter point inwards along the normal until the distance to the surface is no longer increasing, selecting that potential location as an isocenter location.

In yet other embodiments, a pre-processing step is performed including smoothing a target surface using a filter function.

According to embodiments of the present invention, the filter function uses a 3D Gaussian filter kernel.

According to a further aspect of the present invention, there is provided a dose planning system for determining isocenter locations in a target volume for use at a radiation therapy system, the radiation therapy system comprising a radiation therapy unit having a fixed radiation focus point, wherein a spatial dose distribution surrounding the focus point can be changed, wherein radiation is directed to the focus point. The dose planning system comprises a calculation module for calculating a curvature of the target surface based on an obtained a target volume of a region of a patient to be treated during a treatment of a patient in a radiation therapy unit, the target volume, for example, being modeled as a three-dimensional voxel representation. A first isocenter location module is configured to perform a first isocenter location procedure including: selecting starting voxels on the surface of the target based on selection curvature criteria, evaluating potential isocenter locations along normal directions of the surface and respective isodistance surfaces in respective starting voxels in a direction inwards from the surface, wherein the normal directions are subsequently calculated from the surface of the target to respective isodistance surfaces inwards from respective surfaces; and selecting a location along the normal directions for placing of an isocenter. A second isocenter location module is configured to perform a second isocenter location procedure including: identifying a median axis of the target volume or center point of the target volume, placing isocenters at locations along the median axis, placing isocenters in the target volume based on a distance to existing isocenters and to the target surface. The dose planning system is configured to provide an isocenter location distribution in the target based on the isocenters placed in the target volume in the first and second isocenter location procedures.

An optimized dose plan determined by means of the present invention may be transferred to a radiation therapy system for use in the treatment of the patient. The dose plan determined by the invention may also or alternatively be used as input in a treatment optimization procedure where the number of isocenters, and position of the isocenters defined during the volume filling according to the invention serves as basis in an optimization of the beam-on time of all the radiation fields at each isocentre position.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

With reference to FIGS. 1-5, an exemplary radiation therapy device in which a treatment plan developed using the present invention can be used for treatment of a patient. However, as been described above, the present invention may also be used in radiation therapy device using a linear accelerator, which irradiates a tumor with high-energy particles (e.g., photons, electrons, and the like). Still another radiation therapy device, a cyclotron, uses protons and/or ions.

Figure 1:
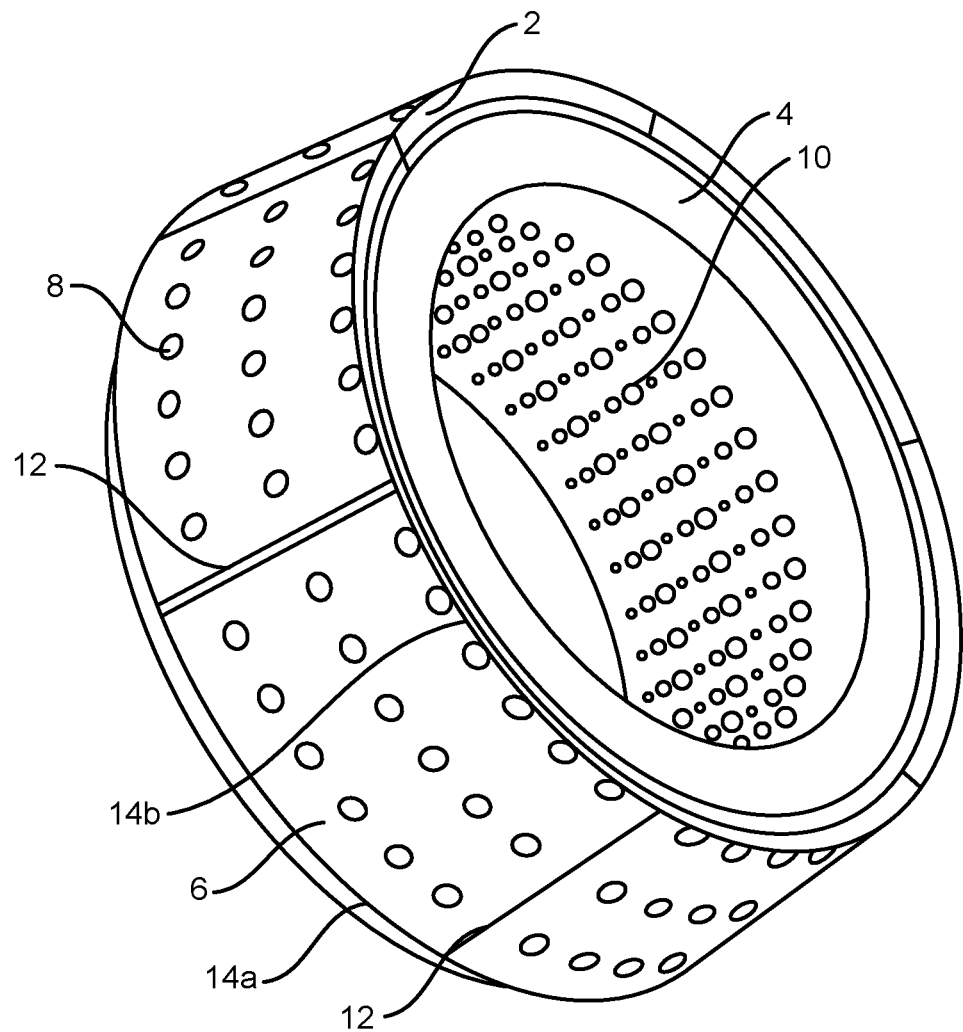
FIG. 1 is a perspective view of an assembly comprising a source carrier arrangement surrounding a collimator body, in accordance with an embodiment of the invention.

FIG. 1 is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of the channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4 but are instead movable back and forth along an imaginary line drawn from the center of the shorter curved side 14b to the center of the longer curved side 14a. Such a translation displacement has the effect of a transformation of coordinates in which the new axes are parallel to the old ones.

As can be seen from FIG. 1 there is a larger number of internal mouths 10 or holes of the collimator passages than the number of apertures 8 for receiving radioactive sources. In this particular case there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus. The diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

Figure 2:
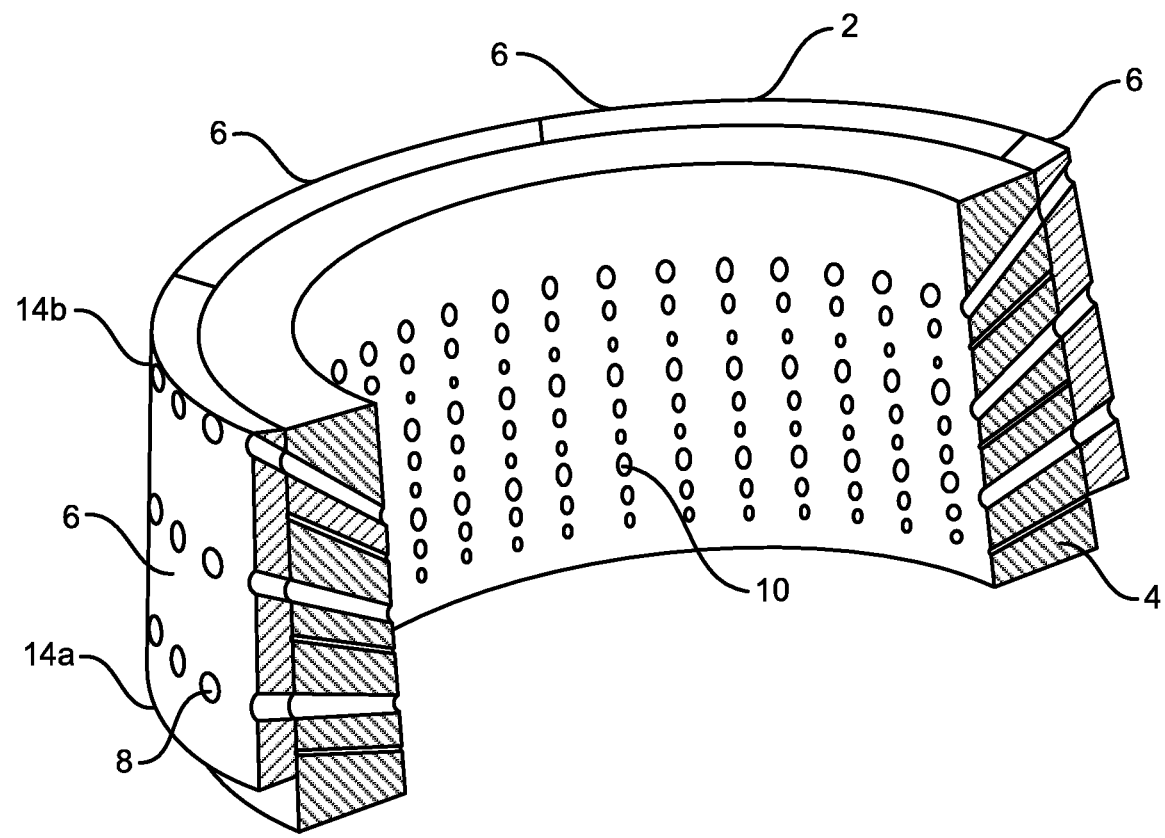
FIG. 2 is sectional view in perspective of the assembly shown in FIG. 1.

FIG. 2 is sectional view in perspective of the assembly shown in FIG. 1. The same reference numerals are used for details which are the same as in FIG. 1. This also applies to the following FIGS. 3 and 4.

Figure 3:
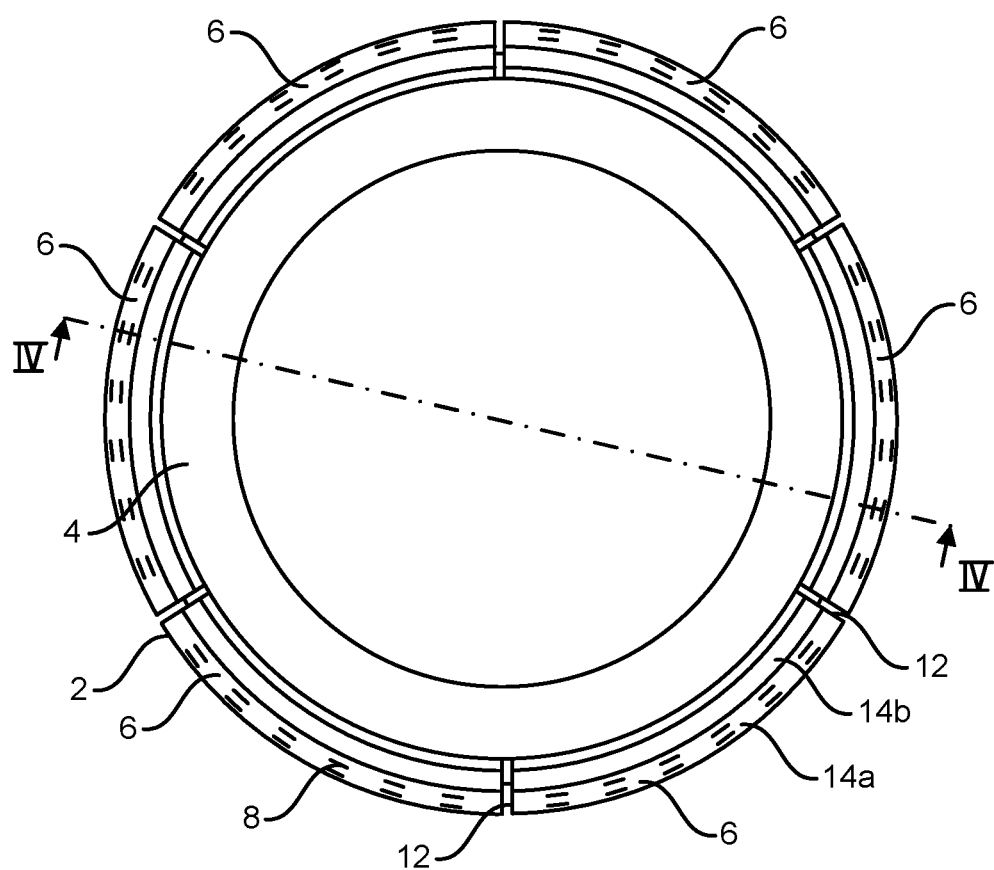
FIG. 3 is a view from the backside of the assembly shown in FIG. 1.

FIG. 3 is a view from the backside of the assembly shown in FIG. 1. This is the side with smaller diameter, while the other side, having a larger diameter, is the front or patient side, i.e. where the patient's body is introduced.

Figure 4:
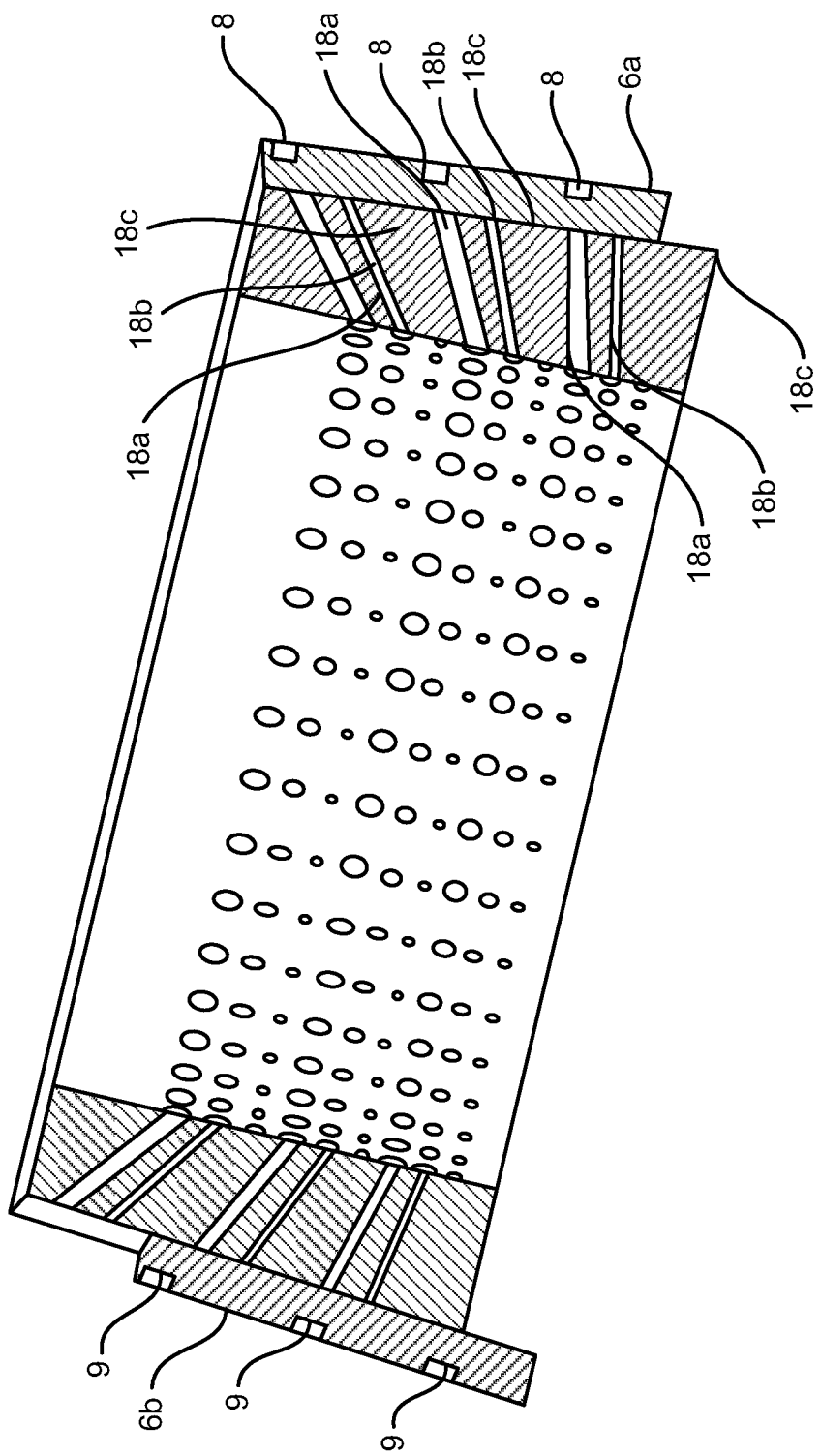
FIG. 4 is a view in cross-section along line Iv-Iv in FIG. 3.

FIG. 4 is a view in cross-section along line Iv-Iv in FIG. 3. Thus, in FIG. 4 two segments 6a and 6b are shown. Starting with one of the segments 6a, in this view it can be seen that there are nine collimator passages 18a-18c available for three radioactive sources 9 contained in a respective aperture 8 in the source carrier arrangement. The sizes of the collimators 18a-18c are arranged in an alternating sequence, such as for instance, the first collimator passage 18a providing a beam of 16 mm in diameter, the second collimator passage 18b providing a beam of 8 mm in diameter, the third collimator passage 18c providing a beam of 4 mm in diameter, the fourth collimator passage 18a starting the sequence all over by providing a beam of 16 mm in diameter, etc. However, the collimator passages 18a-18c could, alternatively, be arranged in another order, e.g. to provide the sequence 16 mm, 4 mm, 8 mm. In the figure the apertures 8 of the source carrier arrangement are arranged in register with the first, fourth and seventh collimator passages 18a, or rather their respective inlets, the collimator passages all providing a beam of 16 mm in diameter at the focus. Each segment may be individually displaced in a straight direction as is illustrated with the double-headed arrow in order to select another group of collimator passages, i.e. another beam diameter size for any segment. If the segment is displaced so that the radioactive sources 9 face a surface in between the collimator passages, those radioactive sources will be shut off, i.e. essentially no or only a minimum radiation from those sources will reach the focus. A segment may also like the segment 6b in FIG. 4 be displaced to such an extent that one of the three shown apertures will be located beside and outside of the first or ninth collimator passage. This allows of the possibility to arrange only two of the three radiation sources 9 in register with two collimator passages. Thus, this and other embodiments do not only enable that differently sized beams are simultaneously directed from different directions toward a common focus, but also that different numbers of beams may simultaneously be directed from different directions.

As can be seen in FIG. 4 the nine collimator passages 18a-18c are arranged at somewhat different angles in order for the beams to be directed to the common focus, regardless of which collimator passage or passages that are used at the moment. The angle of extension direction of the first to the last collimator passage having the same cross-section is, in this case, at least 30°.

Figure 5:
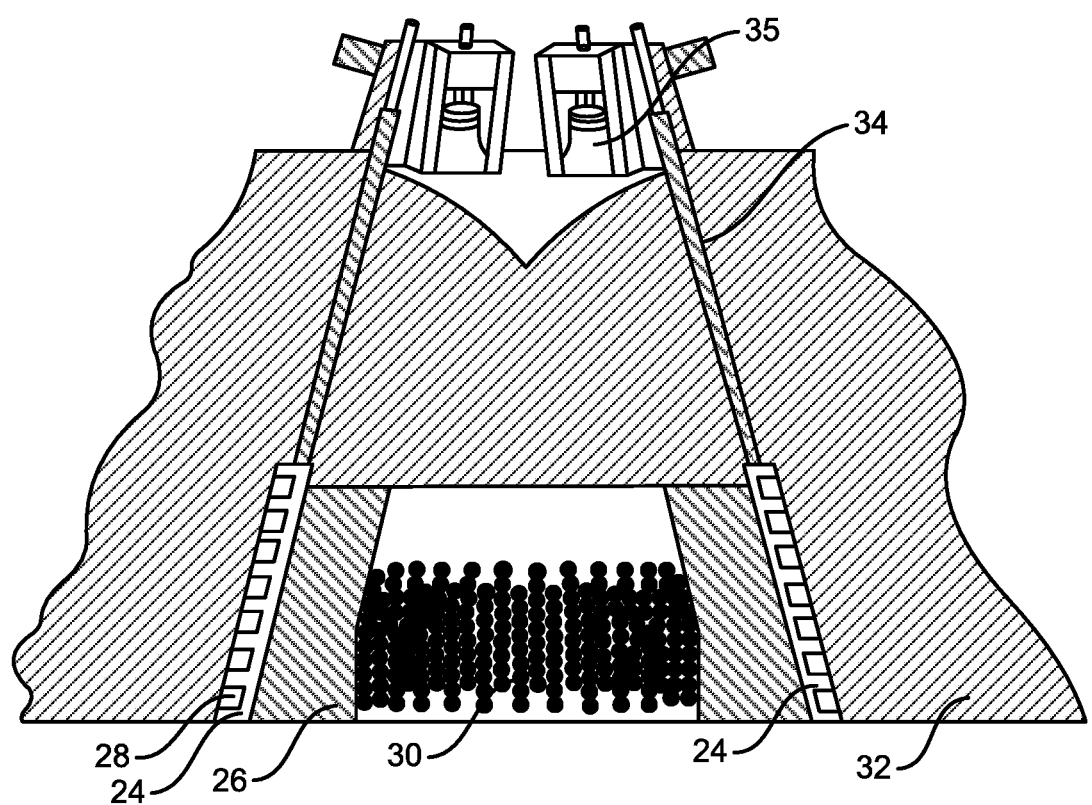
FIG. 5 is a sectional view of an assembly of the type shown in FIGS. 1-4, the assembly being illustrated with an actuating mechanism and a rear radiation protection structure.

FIG. 5 is a sectional view of an assembly of the type shown in FIGS. 1-4, the assembly being illustrated with an actuating mechanism and a rear radiation protection structure. Accordingly, a source carrier arrangement having a plurality of segments 24 is provided. Each segment 24 has a number of apertures 28 in which sources are inserted. The segments 24 are arranged around a collimator body 26 having collimator passages (not shown) with mouths 30 directing radiation beams towards a focus.

The segments are surrounded by a rear radiation protection structure 32, so as to minimize or eliminate leakage of radiation to the nursing personnel. The rear protection structure 32 is dimensioned and made of a suitable material, such as casting material, accordingly. A front radiation protection structure (not shown) is suitably also provided, preferably of smaller dimension so as to facilitate access to the treatment space, but with a high-density material, such as lead, tungsten or depleted uranium.

An actuating mechanism is provided for displacing the segments in a linear direction of motion. The maximum displacement distance for a segment may e.g. be 60 mm, however larger or smaller distances are also conceivable. The actuating mechanism comprises a number of supporting rods or arms 34, each arm being connected to a respective segment 24. The arms 34 extend through a respective bore in the rear radiation protection structure 32 and are movable along their direction of elongation. The arm and the bore are designed so as to form a labyrinth passage having different portions of overlapping diameters, thereby minimizing or eliminating the escape of hazardous radiation through the bore. Each arm is individually controlled by means of a respective rotational electrical motor. The electrical motor has a high resolution with a positioning encoder and a ball roller screw enabling a precise linear positioning of the arm 34 and the segment 24. A spring means 35 is arranged to affect the arms and ensure that they displace the segments so that the radioactive sources will be in a complete shut-off position in case of power failure. The arms 34 may be disconnected from the segments 24, when the segments are to be provided with new radioactive sources. In such case the loading is suitably done through channels (not shown) provided in one area of in the rear radiation protection structure 32. The loading procedure may be performed in a conventional manner as in the prior art, e.g. a procedure corresponding to the one used in connection with Leksell Gamma Knife® Perfexion and Leksell Gamma Knife® Icon. However, alternative procedures are also conceivable.

Figure 6:
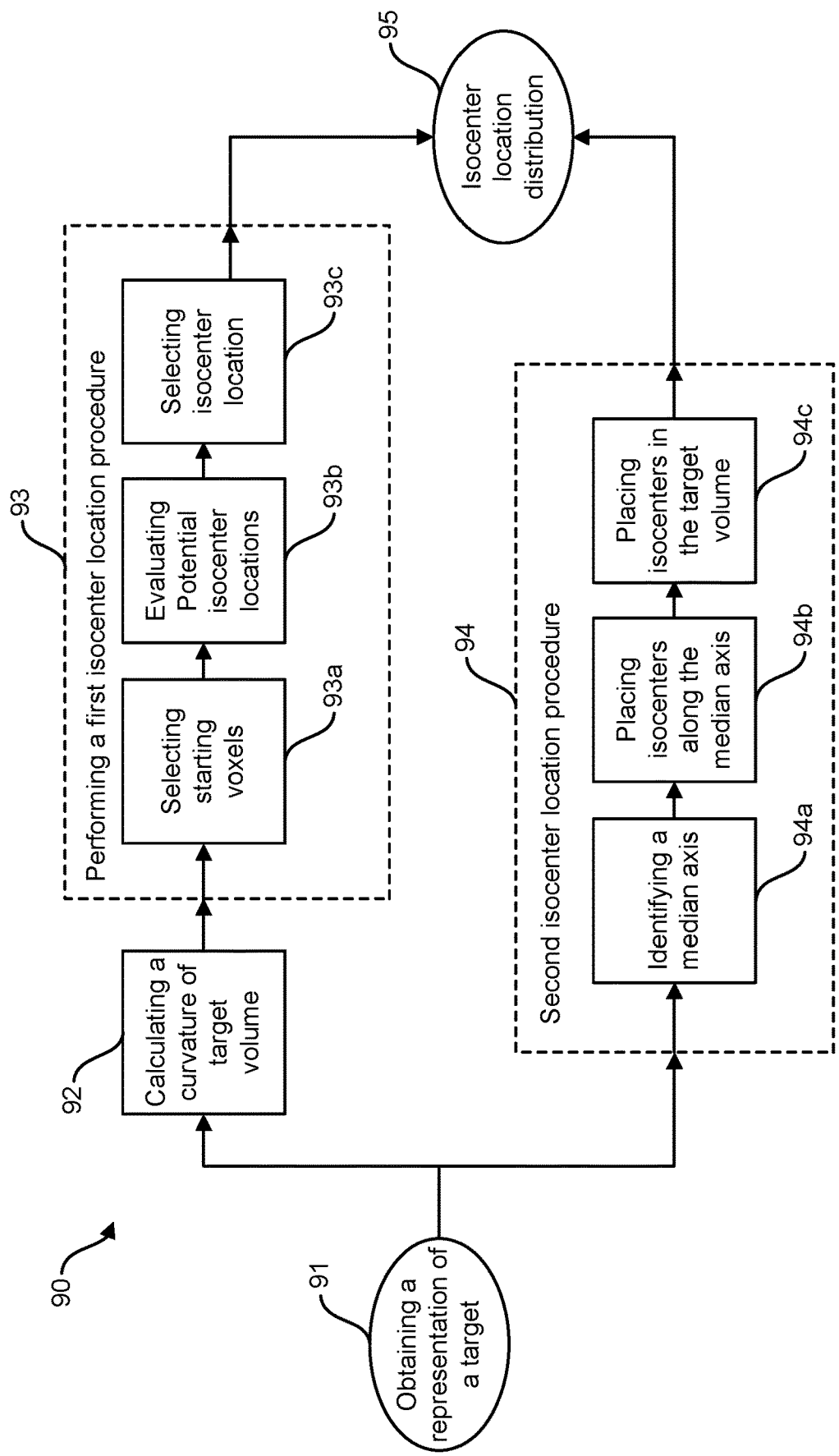
FIG. 6 is a flow chart illustrating an embodiment of the present invention.

With reference now to FIG. 6, an embodiment of the method 90 according to the present invention will be described. Isocenter positions are determined according to two separate geometrical attributes of the target, the curvature and the skeleton. The curvature of the target is considered to enable a conformal dose distribution, and also the shape and bulk of the target to fill the volume with suitable number of isocenters.

First, at step 91, a representation of a target is obtained, for example, a target volume, defined by a binary three-dimensional image (i.e. a voxel space).

At step 92, the extrinsic curvature is calculated from the signed distance transform of the target volume mask. The minimum curvature radius is capped to a value defined by the minimum scale on which the Leksell Gamma Knife is able to shape the dose.

At step 93, performing a first isocenter location procedure including: selecting starting voxels on the surface of the target based on selection curvature criteria in step 93a, evaluating potential isocenter locations along normal directions of the surface and respective isodistance surfaces in respective starting voxels in a direction inwards from the surface, wherein the normal directions are subsequently calculated from the surface of the target to respective isodistance surfaces inwards from respective surface in step 93b, and selecting a location along the normal directions for placing of an isocenter 93c. Thus, the candidate points are along the integrated normals to the isodistance surfaces with:

Isodistance=0-surface being the target surface.

First, that normal is followed a certain step length to the next generated isodistance surface. A new normal is then calculated and followed a certain step length to the next isodistance surface and so on. In general, the line that we follow will be bent off from line along the surface normal.

In step 94, performing a second isocenter location procedure including: identifying a median axis of the target volume in step 94a, placing isocenters at locations along the median axis in step 94b, and placing isocenters in the target volume based on a distance to existing isocenters and to the surface in step 94c, In step 95, an isocenter location distribution for the target is provided based on the isocenters placed in the target volume in the first and second isocenter location procedures 93 and 94.

Figure 7:
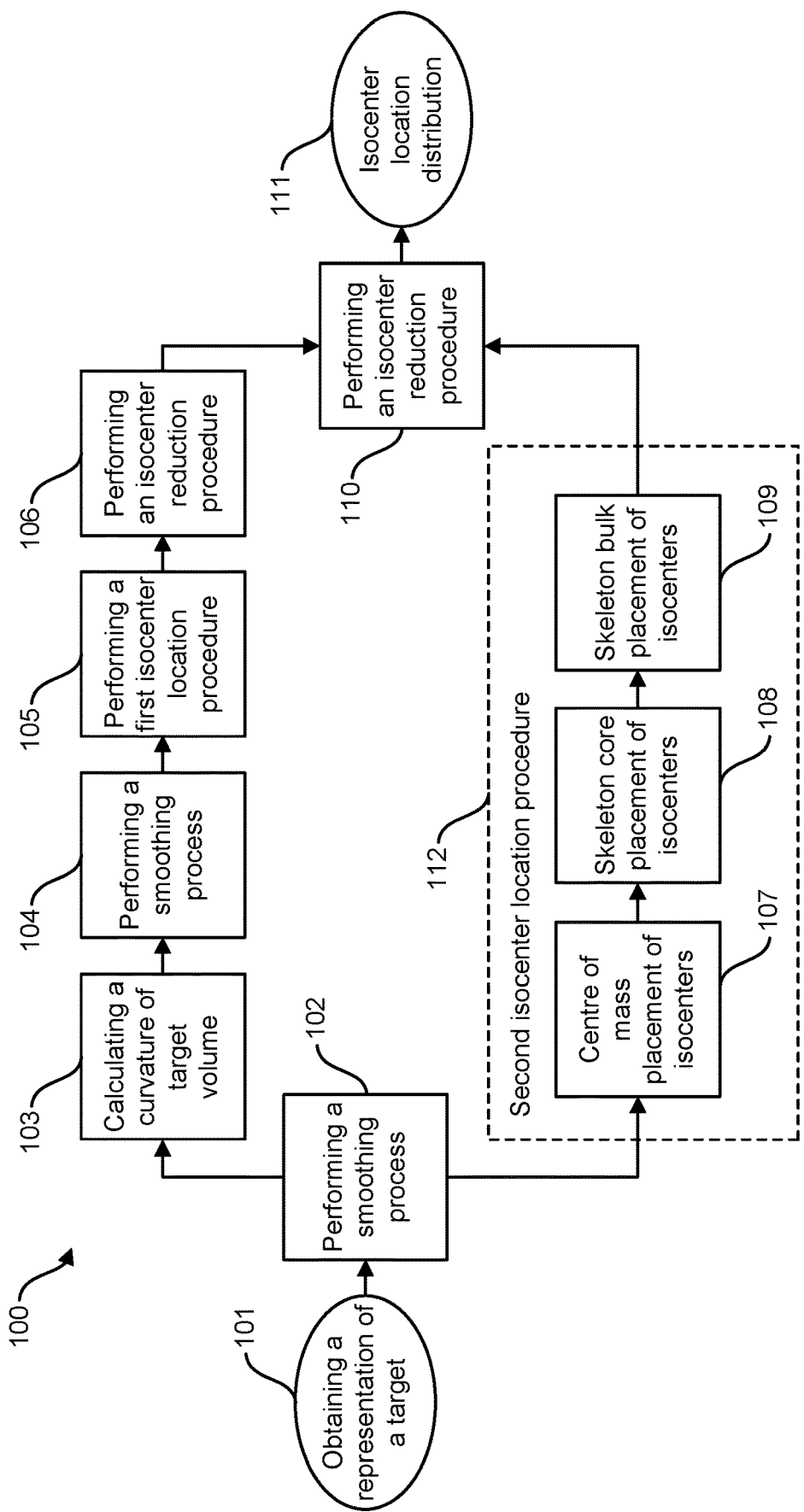
FIG. 7 is a flow chart illustrating a further embodiment of the present invention.

With reference now to FIG. 7, a method 100 according to the present invention will be described. Isocenter positions are determined according to two separate geometrical attributes of the target, the curvature and the skeleton. The curvature of the target is considered to enable a conformal dose distribution, and also the shape and bulk of the target to fill the volume with suitable number of isocenters.

First, at step 101, a representation of a target is obtained, for example, a target volume, defined by a binary three-dimensional image (i.e. a voxel space). Thereafter, at step 102, pre-preprocessing step is performed. In embodiments of the present invention, the target volume surface or mask is smoothed using a 3D Gaussian kernel. In order to be able to shape the dose distribution according to the target surface, a part of the method is directed to positioning isocenters close to the surface. The isocenters will be positioned close to highly geometrically complex surfaces where the need to control the shape of the dose distribution is the highest. The complexity is quantified by the extrinsic curvature of the surface.

At step 103, the extrinsic curvature is calculated from the signed distance transform of the target volume mask. The minimum curvature radius is capped to a value defined by the minimum scale on which the Leksell Gamma Knife is able to shape the dose.

At step 104, the curvature is smoothed, for example, using a 3D Gaussian kernel.

At step 105, a first isocenter location procedure is performed. The isocenters are to be placed at a certain distance from the surface in regions with the highest curvature. This is achieved by first selecting candidates on the surface where the curvature radius is less than a certain threshold. Candidates are then selected iteratively based on maximum curvature. When a candidate isocenter position has been selected it is iteratively being propagated in the normal direction of the surface (inwards) in incemental steps. The normal vector is updated for each step. Propagation is stopped when either of the following two conditions is being met:

1. The total distance along the normal is greater or equal to a distance proportional to the curvature radius of the surface at the candidate starting position. The goal is to place an isocenter that gives a dose distribution conformal to the surface closest to the isocenter.

2. The distance to the surface is no longer increasing. This means the isocenter is being propagated closer to another part of the surface, restricting the possible influence of the isocenter in the vicinity of the candidate starting position.

Figure 12:
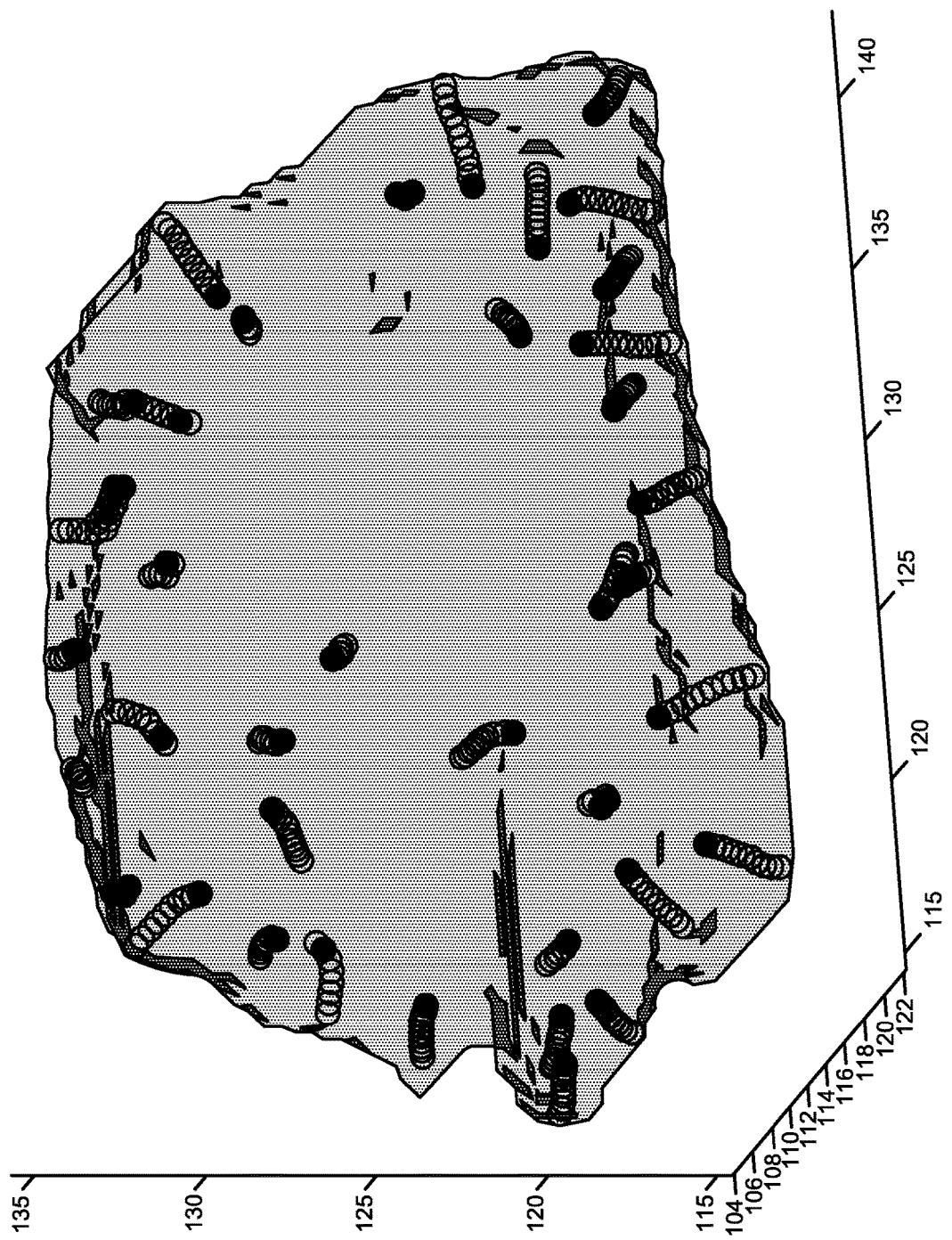
FIG. 12 shows details of the isocentre location procedure according to the present invention.

In FIG. 12, it is illustrated a procedure for evaluating potential isocenter locations (circles) by propagating surface points along a surface normal a distance proportional to the curvature radius at given surface points (dots).

In step 106, an isocenter reduction procedure is performed. In one embodiment, all candidate positions within a certain radius of the selected candidate starting position are excluded from further selection. In the second part of the method, where a second isocenter location procedure 112 is performed, the shape of the target is used for the filling procedure.

In step 107, a centre of mass placement of isocenters is performed. For very small volumes with irregular shape for which all the voxels are surface voxels, the other algorithms may either fail to generate any isocenter or generate suboptimal isocenters. To handle this special case an isocenter is positioned at the centre of mass of the target voxel mask.

Figure 8:
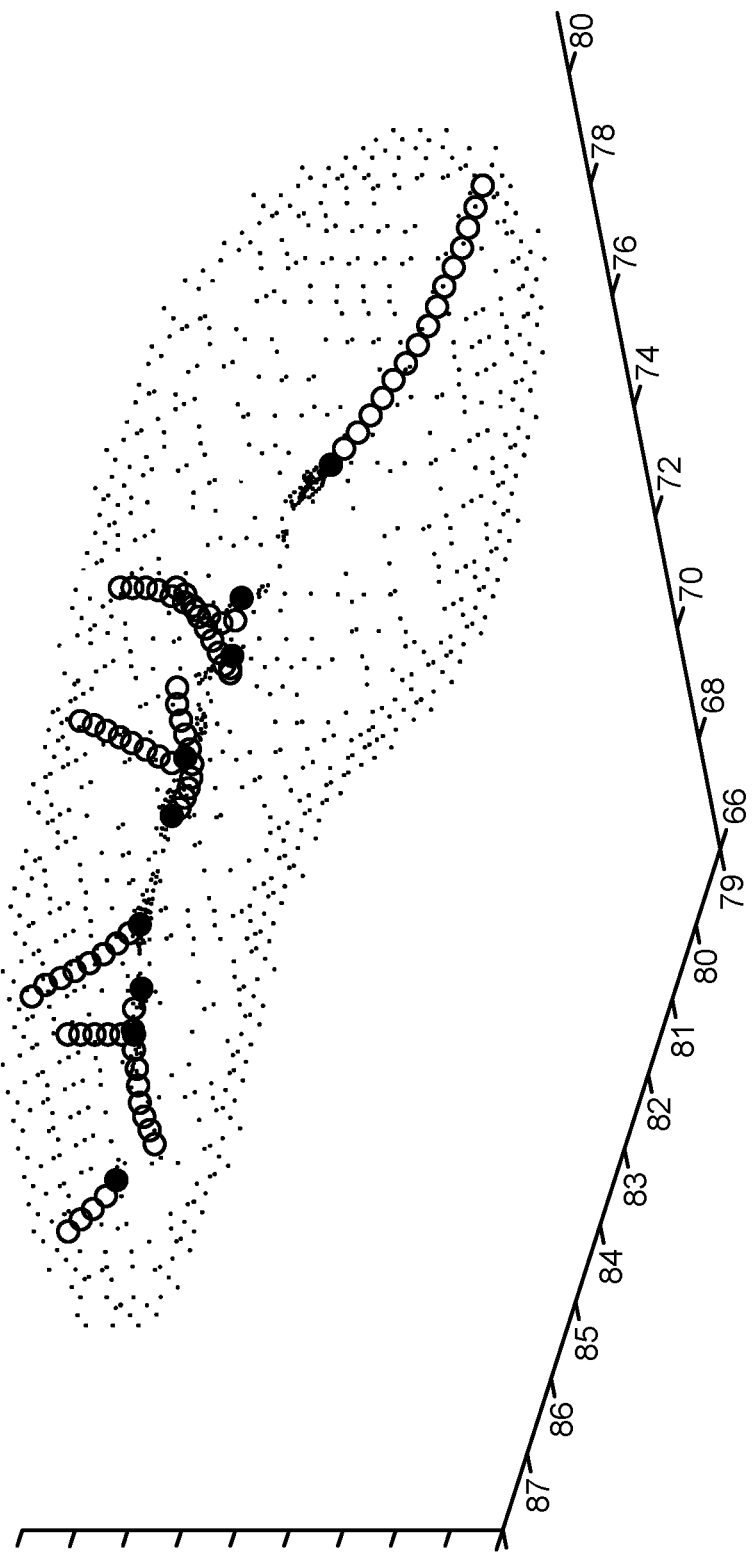
FIG. 8 shows skeleton core placement of isocenters according to the present invention.

In step 108, a skeleton core placement of isocenters is performed. The skeleton core isocenters will be located as far as possible from the surface, along the median line. This is illustrated in FIG. 8. This will allow for the largest possible dose contribution to the target volume while keeping dose outside the target low. All points on the surface are being propagated in small steps in the normal direction until the distance to the surface is no longer increasing (i.e. it is approaching another side of the volume), see dots indicated with "o" in FIG. 8. The resulting skeleton core candidate points will be clustered along the median line of the target volume, see dots "filled o" in FIG. 8. The isocenter with the maximum distance to the surface is then iteratively selected from these points, while in each new selection applying a minimum distance policy based on the already selected points.

Figure 13:
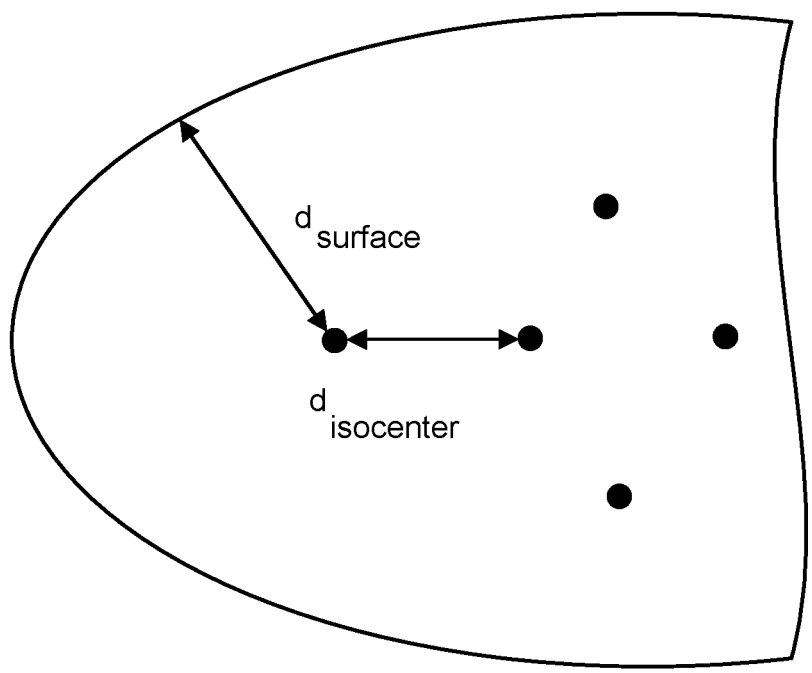
FIG. 13 shows details of the isocentre location procedure according to the present invention.

In step 109, a skeleton bulk placement of isocenters is performed. The skeleton core will follow the median line of the target volume. To be able to cover regions that are not close to the median line, the bulk skeleton algorithm will position isocenters based on the distance to other isocenters and the surface. In FIG. 13 it is illustrated how isocenters are placed in a target volume based on a relative distance to existing isocenters and to the surface, including determining the relative distance to an isocenter as the distance from a potential isocenter location to that isocenter divided by an isocenter cut off distance constant, and determining the relative distance to the surface as the Euclidian distance from the potential isocenter location divided by a surface cut off distance constant. That is, the minimum of the relative distance to a closest isocenter is compared
and the relative distance to the surface for each potential location with corresponding minimum relative distance in all other potential locations, and selecting the maximum relative distance as an isocenter location.

Isocenters already generated by the centre of mass algorithm and the core skeleton algorithm are are taken into consideration.

According to an embodiment, the selection of isocenters are made iteratively based on the relative distance to existing isocenters and the surface. The relative distance to other isocenters is the distance from a point to the closest isocenter, divided by an isocenter cut off distance constant. The relative distance to the surface is given by the Euclidian distance divided by a surface cut off distance constant. These two relative distances are calculated in each point or voxel in the target volume. The minimum of the two relative distances in each point or voxel is compared with the corresponding minimum relative distances in all other points or voxels. The point or voxel with the maximum relative distance is selected as an isocenter. When there are no more points or voxels with a relative distance greater than a pre-determined constant, the algorithm stops. This means that the distance to either the closest isocenter or the surface is smaller than the respective cut off distance in every point or voxel.

The procedure may thus be as follows:

Maximum relative distance: $d\max = \max(d_p)$, for all $p$

Relative distance in point or voxel p:

$$d_p = \min(d_{p,surface}/COD_{surface}, d_{p,isocenter}/COD_{isocenter}),$$

where
$d_{p,surface}$ is the distance to the closest point or voxel on the surface,
$d_{p,isocenter}$ is the distance to the closest isocenter,
$COD_{surface}$ is the minimal distance to the surface for new skeleton bulk isocenters, and
$COD_{isocenter}$ is the minimal distance to the closest isocenter for new skeleton bulk isocenters The independent first and second isocenter location procedures 105 and 112 may position isocenters fairly close to each other. Isocenters that are too close to another isocenter will have limited individual influence on the dose distribution and are redundant. Therefore, in step 110, an isocenter reduction procedure may be performed. Isocenters which are within a certain radius of another isocenter will be removed. The order of priority is, starting with the highest: skeleton centre of mass, skeleton core, skeleton bulk, curvature or the first isocenter location procedure.

Figure 14:
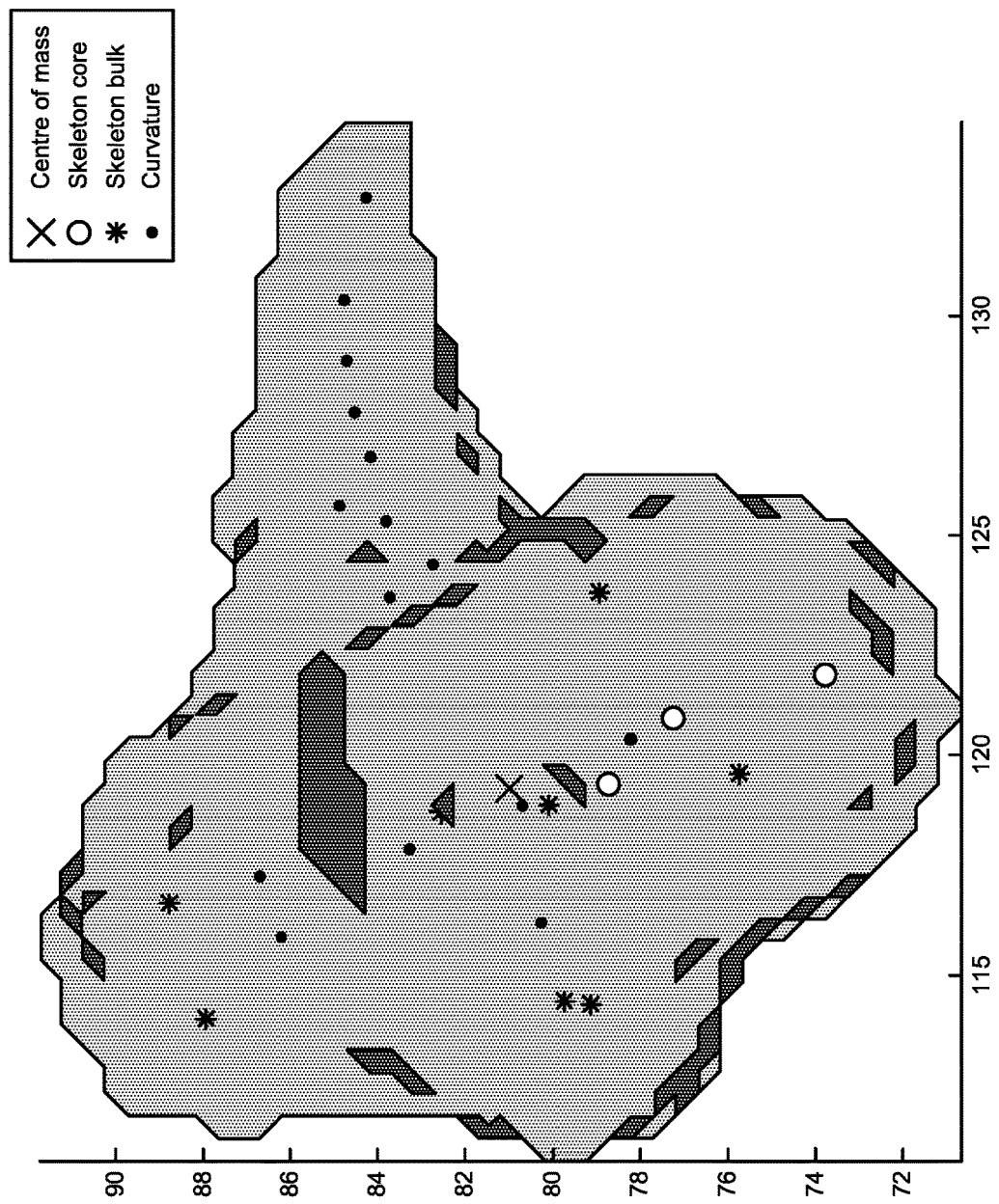
FIG. 14 shows details of the isocentre location procedure according to the present invention.

In FIG. 14, it is illustrated how the first and second isocenter location procedures combines the different algorithms to generate all the isocenter positions. Note that the described isocenter reduction algorithm has been applied to reduce the number of isocenters. In FIG. 14, "X" denotes centre of mass, "o" skeleton core, "*" skeleton bulk and "dots" curvature.

Then, at step 111, a final isocenter location distribution can be provided for the target based on the isocenters placed in the target volume in the first and second isocenter location procedures.

Figure 9:
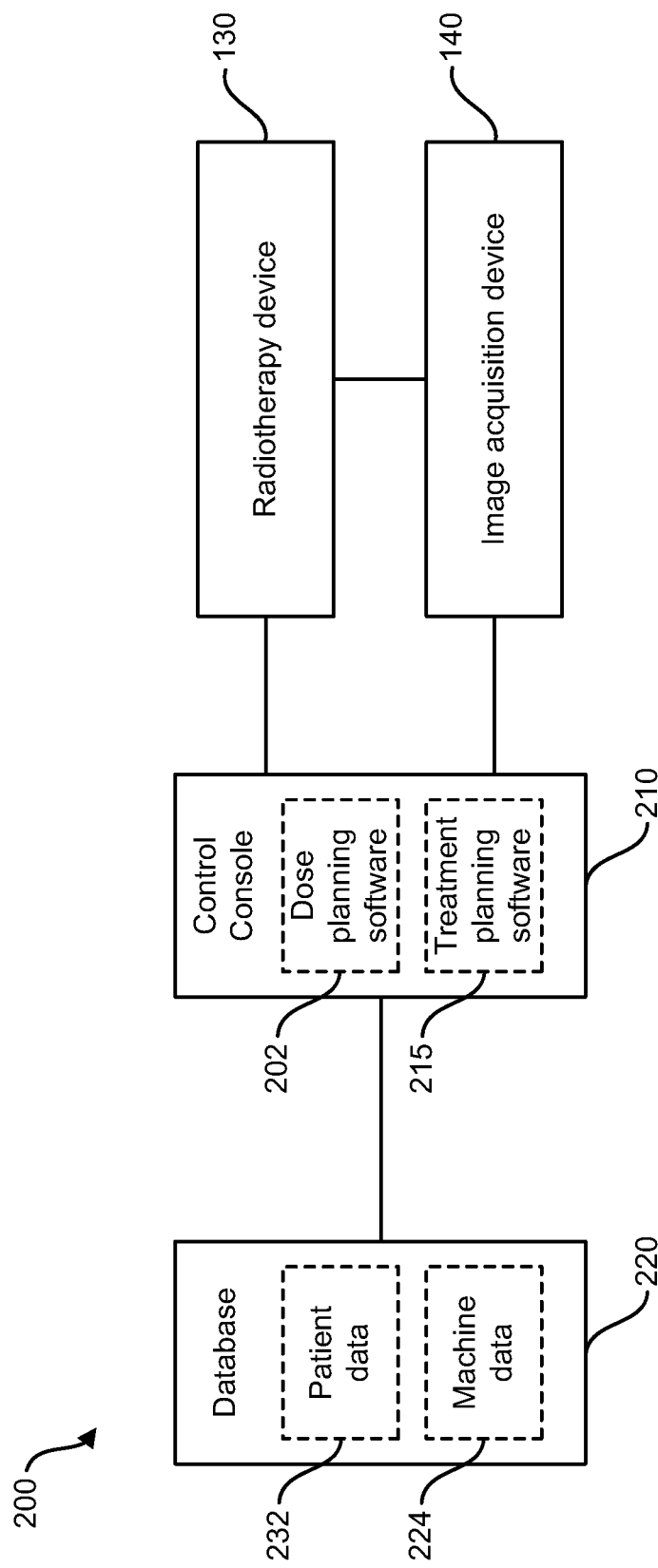
FIG. 9 shows a system in accordance with embodiments of the present invention.

Turning now to FIG. 9, a dose planning computer structure or software 202 in which the method according to the present invention may be implemented will be described. The dose planning structure or software 202 may be included in a radiation therapy system 200 as shown in FIG. 9. As shown in FIG. 9, radiation therapy system 200 may include a control console 210, a database 220, a radiation therapy device 130. The control console 210 may include hardware and software components to control radiation therapy device 130 and other equipment such as an image acquisition device 140 and/or to perform functions or operations such as treatment planning using a treatment planning software and dose planning using dose planning computer structure or software 202, treatment execution, image acquisition, image processing, motion tracking, motion management, or other tasks involved in a radiation therapy process. The hardware components of control console 210 may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); or other suitable hardware. The software components of control console 210 may include operation system software, application software, etc. For example, as shown in FIG. 9, control console 210 includes the dose planning computer structure or software 202 and a treatment planning/delivery software 215 that both may be stored in a memory/storage device of control console 210. Software 202 and 215 may include computer readable and executable codes or instructions for performing the processes described in detail in this application. For example, a processor device of control console 210 may be communicatively connected to a memory/storage device storing software 202 and 215 to access and execute the codes or instructions. The execution of the codes or instructions may cause the processor device to perform operations to achieve one or more functions consistent with the disclosed embodiments.

The dose planning computer structure or software 202 be configured to execute the methods described herein, for example, the methods described with reference to FIGS. 6 and 7.

Figure 10:
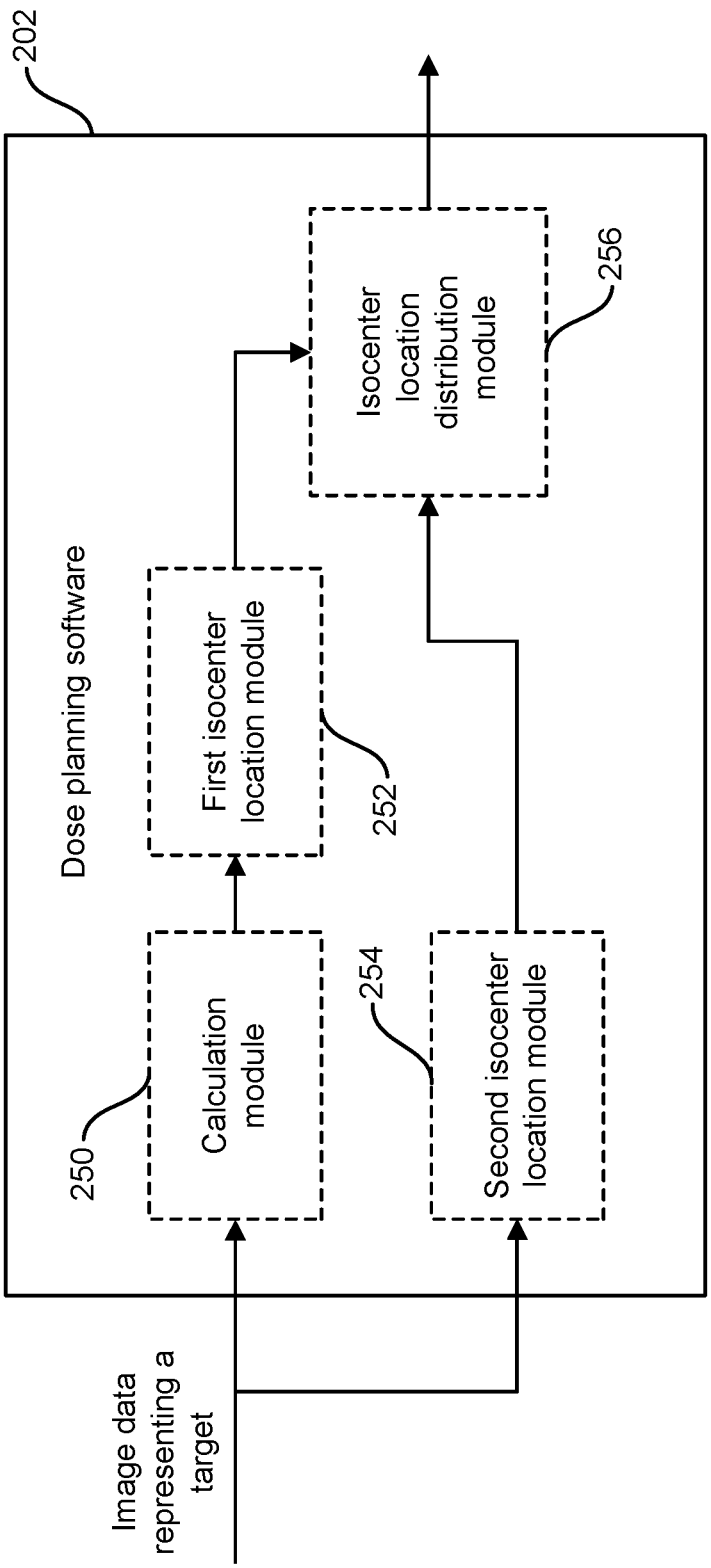
FIG. 10 shows a dose planning software structure according to embodiments of the present invention.

In FIG. 10, an embodiment of the dose planning structure according to the present invention is described.

An image representation of a target is obtained, for example, a target volume, defined by a binary three-dimensional image (i.e. a voxel space), for example, from the database 220, or the Image acquisition device 140.

In a calculation module 250, the extrinsic curvature is calculated from the signed distance transform of the target volume mask. The minimum curvature radius is capped to a value defined by the minimum scale on which the Leksell Gamma Knife is able to shape the dose.

In a first isocenter location module 252, isocenters are localized in the target based on the curvature, including: selecting starting voxels on the surface of the target based on selection curvature criteria, evaluating potential isocenter locations along normal directions of the surface and respective isodistance surfaces in respective starting voxels in a direction inwards from the surface, wherein the normal directions are subsequently calculated from the surface of the target to respective isodistance surfaces inwards from respective surfaces, and selecting a location along the normal directions for placing of an isocenter. Thus, the candidate points are along the integrated normals to the isodistance surfaces with:

Isodistance=0-surface being the target surface.

First, that normal is followed a certain step length to the next generated isodistance surface. A new normal is then calculated and followed a certain step length to the next isodistance surface and so on. In general, the line that we follow will be bent off from the line along the surface normal.

In a second isocenter location module 254, an isocenter location procedure is performed based on the obtained image representation of a target including: identifying a median axis of the target volume, placing isocenters at locations along the median axis, and placing isocenters in the target volume based on a distance to existing isocenters and to the surface.

In an isocenter location distribution module 256, the isocenter location distribution for the target is provided based on the isocenters placed in the target volume in the first and second isocenter location procedures performed in modules 252 and 254. The isocenter location distribution in conjunction with e.g. an optimization method may then be used for determining the shots to be delivered. That is, it may be configured to determine shots to be delivered during the treatment, each shot being associated with an isocenter and being modelled by a spatial dose volume distribution of radiation, the shape of the spatial distribution depending on the specific collimator setting, including: evaluating each isocenter and predetermined angle in a predetermined angle range based on predetermined conditions; selecting at least a specific collimator and sector setting for each isocenter and angle based on the evaluation; calculating a dose rate for the selected isocenters; repeating the steps evaluating, selecting and calculating until at least one stop criterion has been reached, wherein a final set of isocenters and angles are provided.

The final set of isocenters and angles may thereafter be in treatment planning, for example, in the treatment planning software 215. Further, the dose planning software 202 may be configured to evaluate a predetermined number of columns in a dose rate matrix for each isocenter and predetermined angle in a predetermined angle range based on predetermined conditions, wherein each column includes a specific collimator and sector setting; select at least one column for each isocenter and angle based on the evaluation; calculate the dose rate matrix including the selected isocenters; and repeat the steps evaluating, selecting and calculating until at least one stop criteria has been reached, wherein a final set of isocenters and angles are provided. Thereafter, the final set of isocenters and angles may be used in treatment planning in the treatment planning software 215.

Figure 11:
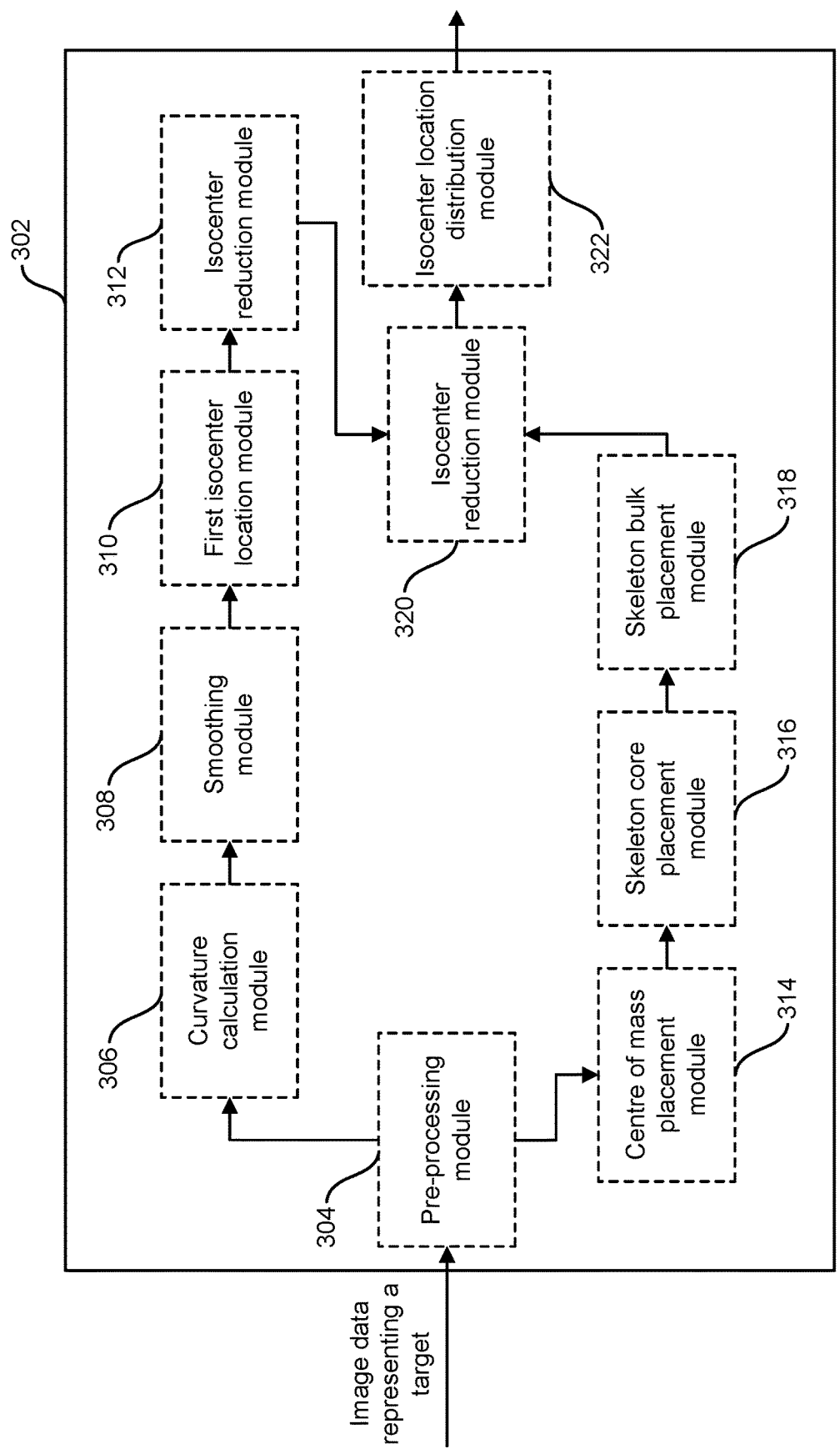
FIG. 11 is a flow chart illustrating a further embodiment of the present invention.

With reference now to FIG. 11, a further embodiment of the dose planning module 302 according to the present invention will be described.

An image representation of a target is obtained, for example, a target volume, defined by a binary three-dimensional image (i.e. a voxel space) from the database 220 or the image acquisition device 140.

In a pre-preprocessing module 304, the target volume surface or mask is smoothed using a 3D Gaussian kernel. In order to be able to shape the dose distribution according to the target surface, a part of the method is directed to positioning isocenters close to the surface. The isocenters will be positioned close to highly geometrically complex surfaces where the need to control the shape of the dose distribution is the highest. The complexity is quantified by the extrinsic curvature of the surface.

In curvature calculation module 306, the extrinsic curvature is calculated from the signed distance transform of the target volume mask. The minimum curvature radius is capped to a value defined by the minimum scale on which the Leksell Gamma Knife is able to shape the dose.

In a smoothing module 308, the curvature is smoothed, for example, using a 3D Gaussian kernel.

In a first isocenter location module 310, a first isocenter location procedure is performed. The isocenters are to be placed at a certain distance from the surface in regions with the highest curvature. This is achieved by first selecting candidates on the surface where the curvature radius is less than a certain threshold. Candidates are then selected iteratively based on maximum curvature. When a candidate isocenter position has been selected it is iteratively being propagated in the normal direction of the surface (inwards) in incremental steps. The normal vector is updated for each step. Propagation is stopped when either of the following two conditions is being met:

1. The total distance along the normal is greater or equal to a distance proportional to the curvature radius of the surface at the candidate starting position. The goal is to place an isocenter that gives a dose distribution conformal to the surface closest to the isocenter. Choosing a distance smaller than the covered radius would require more isocenters.

2. The distance to the surface is no longer increasing. This means the isocenter is being propagated closer to another part of the surface, restricting the possible influence of the isocenter in the vicinity of the candidate starting position.

In a reduction module 312, an isocenter reduction procedure is performed. In one embodiment, all candidate positions within a certain radius of the selected candidate starting position are excluded from further selection.

In a centre of mass placement module 314, a placement of isocenters based on a centre of mass calculation is performed. For very small volumes with irregular shape for which all the voxels are surface voxels, the other algorithms may either fail to generate any isocenter or generate suboptimal isocenters. To handle this special case an isocenter is positioned at the centre of mass of the target voxel mask.

In a skeleton core placement module 316, a placement of isocenters based on a skeleton core calculation is performed. The skeleton core isocenters will be located as far as possible from the surface, along the median line. This will allow for the largest possible dose contribution to the target volume while keeping dose outside the target low. All points on the surface are being propagated in small steps in the normal direction until the distance to the surface is no longer increasing (i.e. it is approaching another side of the volume). The resulting skeleton core candidate points will be clustered along the median line of the target volume. The isocenter with the maximum distance to the surface is then iteratively selected from these points, while in each new selection applying a minimum distance policy based on the already selected points.

In a skeleton bulk placement module 318, a placement of isocenters based on a skeleton bulk calculation is performed. The skeleton core will follow the median line of the target volume. To be able to cover regions that are not close to the median line, the bulk skeleton algorithm will position isocenters based on the distance to other isocenters and the surface. Isocenters already generated by the centre of mass algorithm and the core skeleton algorithm are are taken into consideration.

According to an embodiment, the selection of isocenters are made iteratively based on the relative distance to existing isocenters and the surface. The relative distance to other isocenters is the distance from a point to the closest isocenter, divided by an isocenter cut off distance constant. The relative distance to the surface is given by the Euclidian distance divided by a surface cut off distance constant. These two relative distances are calculated in each point or voxel in the target volume. The minimum of the two relative distances in each point or voxel is compared with the corresponding minimum relative distances in all other points or voxels. The point or voxel with the maximum relative distance is selected as an isocenter. When there are no more points or voxels with a relative distance greater than a pre-determined constant, the algorithm stops. This means that the distance to either the closest isocenter or the surface is smaller than the respective cut off distance in every point or voxel.

The procedure may thus be as follows:

Maximum relative distance: $d\text{max} = \max(d_p)$, for all $p$

Relative distance in point or voxel p:

$$d_p = \min(d_{p,surface}/COD_{surface}, d_{p,isocenter}/COD_{isocenter}),$$

where
$d_{p,surface}$ is the distance to the closest point or voxel on the surface,
$d_{p,isocenter}$ is the distance to the closest isocenter,
$COD_{surface}$ is the minimal distance to the surface for new skeleton bulk isocenters, and
$COD_{isocenter}$ is the minimal distance to the closest isocenter for new skeleton bulk isocenters The independent location procedures based on curvature and skeleton, respectively, may position isocenters fairly close to each other. Isocenters that are too close to another isocenter will have limited individual influence and are redundant. Therefore, in an isocenter reduction module 320, an isocenter reduction procedure may be performed. Isocenters which are within a certain radius of another isocenter will be removed. The order of priority is, starting with the highest: skeleton centre of mass, skeleton core, skeleton bulk, curvature or the first isocenter location procedure.

Then, the isocenter location distribution module 322, a final isocenter location distribution can be provided for the target based on the isocenters placed in the target volume in the first and second isocenter location procedures. The isocenter location distribution may then be used for determining the shots to be delivered. That is, it may be configured to determine shots to be delivered during the treatment, each shot being associated with an isocenter and being modelled by a spatial dose volume distribution of radiation, the shape of the spatial distribution depending on the specific collimator setting, including: evaluating each isocenter and predetermined angle in a predetermined angle range based on predetermined conditions; selecting at least a specific collimator and sector setting for each isocenter and angle based on the evaluation; calculating a dose rate for the selected isocenters; repeating the steps evaluating, selecting and calculating until at least one stop criterion has been reached, wherein a final set of isocenters and angles are provided.

The final set of isocenters and angles may thereafter be in treatment planning, for example, in the treatment planning software 215. Further, the dose planning software 202 may be configured to evaluating a predetermined number of columns in a dose rate matrix for each isocenter and predetermined angle in a predetermined angle range based on predetermined conditions, wherein each column include a specific collimator and sector setting; selecting at least one column for each isocenter and angle based on the evaluation; calculating the dose rate matrix including the selected isocenters; and repeating the steps evaluating, selecting and calculating until at least one stop criteria has been reached, wherein a final set of isocenters and angles are provided. Thereafter, the final set of isocenters and angles may be used in treatment planning in the treatment planning software 215.

As indicated above, control console 210 may be communicatively connected to a database 220 to access data. In some embodiments, database 220 may be implemented using local hardware devices, such as one or more hard drives, optical disks, and/or servers that are in the proximity of control console 210. In some embodiments, database 220 may be implemented in a data center or a server located remotely with respect to control console 210. Control console 210 may access data stored in database 220 through wired or wireless communication.

Database 220 may include patient data 232. Patient data may include information such as (1) imaging data associated with a patient anatomical region, organ, or volume of interest segmentation data (e.g., MRI, CT, X-ray, PET, SPECT, and the like); (2) functional organ modeling data (e.g., serial versus parallel organs, and appropriate dose response models); (3) radiation dosage data (e.g., may include dose-volume histogram (DVH) information); or (4) other clinical information about the patient or course of treatment.

Database 220 may include machine data 224. Machine data 224 may include information associated with radiation therapy device 130, image acquisition device 140, or other machines relevant to radiation therapy, such as radiation beam size, arc placement, on/off time duration, radiation treatment plan data, multi-leaf collimator (MLC) configuration, MRI pulse sequence, and the like.

Image acquisition device 140 may provide medical images of a patient. For example, image acquisition device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, image acquisition device 140 may include an MRI imaging device, a CT imaging device, a PET imaging device, an ultrasound imaging device, a fluoroscopic device, a SPECT imaging device, or other medical imaging devices for obtaining the medical images of the patient.

Radiation therapy device 130 preferably includes a Leksell Gamma Knife®. However, in certain embodiments, the radiation therapy device 130 includes a linear accelerator, which irradiates a tumor with high-energy particles (e.g., photons, electrons, and the like). Still another radiation therapy device, a cyclotron, uses protons and/or ions.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

Embodiments of the present disclosure may be implemented with computer-executable instructions. The computer-executable instructions may be organized into one or more computer-executable components or modules. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

The invention claimed is:

1. A method performed by a radiation therapy system for determining isocenter locations in a target volume, said system comprising a radiation therapy unit having a fixed radiation focus point, wherein a spatial dose distribution surrounding the focus point can be adjusted, wherein radiation is directed to said focus point, said method comprising:
   a) obtaining a target volume of a region of a patient to be treated during a treatment of the patient in the radiation therapy unit;
   b) calculating a curvature of a target surface;
   c) performing a first isocenter location procedure including:
      c1) selecting starting voxels on the surface of the target based on selection curvature criteria;
      c2) evaluating potential isocenter locations along normal directions of the surface of the target and respective isodistance surfaces in respective starting voxels in a direction inwards from the surface of the target, wherein said normal directions are subsequently calculated from the surface of the target to the respective isodistance surfaces inwards from the respective isodistance surfaces;
      c3) selecting a location along said normal directions for placing of an isocenter;
   d) performing a second isocenter location procedure including:
      d1) identifying a median axis of said target volume or center point of said target volume;
      d2) placing isocenters at locations along said median axis;
      d3) placing isocenters in said target volume based on a distance to existing isocenters and to the target surface; and
   e) providing an isocenter location distribution in said target volume based on the isocenters placed in said target volume in said first and second isocenter location procedures.

2. The method according to claim 1, wherein step d) further comprises the step of determining a center of mass of said target volume and placing an isocenter at said center of mass.

3. The method according to claim 1, wherein step d3) further comprises the step of placing isocenters in said target volume based on a relative distance to existing isocenters and to the target surface, including:
   determining the relative distance to an isocenter as a distance from a potential isocenter location to said isocenter divided by an isocenter cut off distance constant; and
   determining the relative distance to the target surface as the Euclidian distance from the potential isocenter location divided by a surface cut off distance constant.

4. The method according to claim 3, further comprising:
   comparing a minimum of the relative distance to a closest isocenter and the relative distance to the target surface for each potential isocenter location with corresponding minimum relative distance in all other potential isocenter locations; and selecting a maximum relative distance as an isocenter location.

5. The method according to claim 4, further comprising: stopping isocenter placement when no further potential isocenter location with the relative distance greater than a pre-determined constant could be found.

6. The method according to claim 1, wherein step c3) further comprises:
   selecting a location along said normal directions for placing of an isocenter when predetermined conditions are met, wherein said predetermined conditions include:
   a total distance along a normal direction is greater or equal to a distance proportional to a curvature radius of the surface at the respective starting voxel; or
   the distance to the surface along the normal direction is no longer increasing.

7. The method according to claim 1, wherein step c1) selecting starting voxels on the surface of the target based on selection curvature criteria, further comprises:
   identifying potential starting voxels on the surface where a curvature radius is less than a predetermined threshold value;
   selecting starting voxels among potential starting voxels by iterative selection based on maximum curvature; and
   disregarding starting voxels that are within a pre-defined distance from already chosen starting voxels.

8. The method according to claim 1, wherein step e) providing an isocenter location distribution in said target based on the isocenters placed in said target volume in said first and second isocenter location procedures further comprises performing an isocenter reduction procedure including:
   determining a radius to adjacent isocenters from a certain isocenter, and removing isocenters being within a pre-determined radius boundary.

9. The method according to claim 8, wherein said step of removing isocenters being within a predetermined radius boundary includes replacing all isocenters within a certain volume surrounding at least one isocenter with a candidate isocenter.

10. The method according to claim 9, wherein said certain volume surrounding at least one isocenter is a radius boundary.

11. The method according to claim 1, wherein step d2) placing isocenters at locations along said median axis further comprises:
    identifying a subset of target voxels as potential isocenter points;
    calculating the normal directions from the target surface inwards for each of the potential isocenter points;
    moving the potential isocenter point inwards a distance along a normal to a new isodistance surface; and
    calculating a normal of the said isodistance surface and moving the potential isocenter point inwards along the normal until the distance to the surface is no longer increasing, selecting that potential isocenter location as an isocenter location.

12. The method according to claim 1, further comprising performing a pre-processing step including smoothing a target surface using a filter function.

13. The method according to claim 12, wherein said filter function uses a 3D Gaussian filter kernel.

14. A dose planning software stored on a processor of a radiation therapy system for determining isocenter locations in a target volume, said system comprising a radiation therapy unit having a fixed radiation focus point, wherein a spatial dose distribution surrounding the focus point can be changed, wherein radiation is directed to said focus point, said dose planning software being configured to execute:
    a) obtaining a target volume of a region of a patient to be treated during a treatment of the patient in the radiation therapy unit;
    b) calculating a curvature of a target surface;
    c) performing a first isocenter location procedure including:
       c1) selecting starting voxels on the surface of the target based on selection curvature criteria;
       c2) evaluating potential isocenter locations along normal directions of the surface of the target and respective isodistance surfaces in respective starting voxels in a direction inwards from the surface of the target, wherein said normal directions are subsequently calculated from the surface of the target to the respective isodistance surfaces inwards from the respective isodistance surface;
       c3) selecting a location along said normal directions for placing of an isocenter;
    d) performing a second isocenter location procedure including:
       d1) identifying a median axis of said target volume or center point of said target volume;
       d2) placing isocenters at locations along said median axis;
       d3) placing isocenters in said target volume based on a distance to existing isocenters and to the target surface; and
    e) providing an isocenter location distribution in said target volume based on the isocenters placed in said target volume in said first and second isocenter location procedures.

15. The dose planning software according to claim 14, wherein step d) further comprises the step of determining a center of mass of said target volume and placing an isocenter at said center of mass.

16. The dose planning software according to claim 14, wherein step d3) further comprises the step of placing isocenters in said target volume based on a relative distance to existing isocenters and to the surface, including:
    determining the relative distance to an isocenter as the distance from a potential isocenter location to said isocenter divided by an isocenter cut off distance constant; and
    determining the relative distance to the surface as the Euclidian distance from the potential isocenter location divided by a surface cut off distance constant.

17. The dose planning software according to claim 16, wherein the dose planning software is configured to execute:
    comparing a minimum of the relative distance to a closest isocenter and the relative distance to the surface for each potential isocenter location with corresponding minimum relative distances in all other potential isocenter locations; and
    selecting a maximum relative distance as an isocenter location.

18. The dose planning software according to claim 17, wherein the dose planning software is configured to execute:
    stopping isocenter placement when no further potential isocenter location with the relative distance greater than a pre-determined constant could be found.

19. The dose planning software according to claim 14, wherein step c3)
    further comprises:

selecting a location along said normal directions for placing of an isocenter when predetermined conditions are met, wherein said predetermined conditions include:

a total distance along a normal direction is greater or equal to a distance proportional to a curvature radius of the surface at the respective starting voxel; or the distance to the surface along the normal direction is no longer increasing.

20. The dose planning software according to claim 14, wherein step c1) selecting starting voxels on the surface of the target based on selection curvature criteria, further comprises:

identifying potential starting voxels on the surface where a curvature radius is less than a predetermined threshold value;

selecting starting voxels among potential starting voxels by iterative selection based on maximum curvature; and disregarding starting voxels that are within pre-defined distance from already chosen starting voxels.

21. The dose planning software according to claim 14, wherein step e) providing an isocenter location distribution in said target based on the isocenters placed in said target volume in said first and second isocenter location procedures further comprises performing an isocenter reduction procedure including:

determining a radius to adjacent isocenters from a certain isocenter, and removing isocenters being within a predetermined radius boundary.

22. The dose planning software according to claim 21, wherein said step of removing isocenters being within a predetermined radius boundary includes replacing all isocenters within a certain volume surrounding at least one isocenter with a candidate isocenter.

23. The dose planning software according to claim 22, wherein said certain volume surrounding at least one isocenter is a radius boundary.

24. The dose planning software according to claim 14, wherein step d2) placing isocenters at locations along said median axis further comprises:

identifying a subset of target voxels as potential isocenter points;

calculating the normal directions from the target surface inwards for each of the potential isocenter points;

moving the potential isocenter point inwards a distance along a normal to a new isodistance surface; and calculating the normal of the said isodistance surface and moving the potential isocenter point inwards along the normal until the distance to the surface is no longer increasing, selecting that potential isocenter location as an isocenter location.

25. The dose planning software according to claim 14, further comprising performing a pre-processing step including smoothing a target surface using a filter function.

26. The dose planning software according to claim 25, wherein said filter function uses a 3D Gaussian filter kernel.

27. A dose planning system in a control console of a radiation therapy system for determining isocenter locations in a target volume, said radiation therapy system comprising a radiation therapy unit having a fixed radiation focus point, wherein a spatial dose distribution surrounding the focus point can be changed by adjusting collimator settings or adjusting the leaves in a MLC (multi leaf collimator), wherein radiation is directed to said focus point, wherein said control console comprises a processor for executing codes of a first isocenter location module and of a second isocenter location module in the dose planning system, wherein:

the processor configures the control console to calculate a curvature of a target surface based on an obtained a target volume of a region of a patient to be treated during a treatment of the patient in the radiation therapy unit, said target volume being modeled as a three-dimensional voxel representation;

the processor configures the first isocenter location module to perform a first isocenter location procedure including: selecting starting voxels on the surface of the target based on selection curvature criteria, evaluating potential isocenter locations along normal directions of the target surface and said respective isodistance surfaces in respective starting voxels in a direction inwards from the target surface, wherein said normal directions are subsequently calculated from the surface of the target to respective isodistance surfaces inwards from the respective isodistance surfaces; and selecting a location along said normal directions for placing of an isocenter;

the processor configures the second isocenter location module to perform a second isocenter location procedure including: identifying a median axis of said target volume or center point of said target volume, placing isocenters at locations along said median axis, placing isocenters in said target volume based on a distance to existing isocenters and to the target surface; and wherein said dose planning system is configured to provide an isocenter location distribution in said target volume based on the isocenters placed in said target volume in said first and second isocenter location procedures.

* * * * *